(12) United States Patent
Uotani et al.

(10) Patent No.: US 8,026,391 B2
(45) Date of Patent: Sep. 27, 2011

(54) POTASSIUM PERFLUOROALKANESULFONATE AND METHOD FOR PRODUCING THE SAME

(75) Inventors: Masakazu Uotani, Akita (JP); Hiroyuki Yatsuyanagi, Yurihonjo (JP); Tsunetoshi Honda, Akita (JP)

(73) Assignees: Mitsubishi Materials Corporation, Tokyo (JP); Mitsubishi Materials Electronic Chemicals Co., Ltd., Akita (JP)

( * ) Notice: Subject to any disclaimer, the term of this patent is extended or adjusted under 35 U.S.C. 154(b) by 608 days.

(21) Appl. No.: 12/063,132

(22) PCT Filed: Sep. 29, 2006

(86) PCT No.: PCT/JP2006/319545
§ 371 (c)(1),
(2), (4) Date: Feb. 7, 2008

(87) PCT Pub. No.: WO2007/037411
PCT Pub. Date: Apr. 5, 2007

(65) Prior Publication Data
US 2009/0143613 A1    Jun. 4, 2009

(30) Foreign Application Priority Data
Sep. 30, 2005 (JP) ................................. 2005-288008

(51) Int. Cl.
*C07C 309/06* (2006.01)
(52) U.S. Cl. ..................................................... 562/113
(58) Field of Classification Search .................... 562/113
See application file for complete search history.

(56) References Cited

U.S. PATENT DOCUMENTS

| | | | |
|---|---|---|---|
| 2,732,398 A | 1/1956 | Brice et al. | |
| 3,919,295 A | 11/1975 | Wechsberg et al. | |
| 4,925,975 A | 5/1990 | Aramaki et al. | |
| 4,927,962 A | 5/1990 | Aramaki et al. | |
| 4,927,964 A | 5/1990 | Naito et al. | |
| 5,498,754 A | 3/1996 | Nakamura et al. | |

FOREIGN PATENT DOCUMENTS

| | | |
|---|---|---|
| CA | 1041035 A1 | 10/1978 |
| JP | 50005325 | 1/1975 |
| JP | 64061452 | 3/1989 |
| JP | 1268671 | 10/1989 |
| JP | 05339768 | 12/1993 |
| SU | 598558 A3 | 3/1978 |

OTHER PUBLICATIONS

The Merck Index, 1989, p. 372-373, #59-60, 11$^{th}$ Edition, Merck & Co., Inc,.
Korean Office Action mailed Feb. 26, 2010 for the corresponding Korean Patent Application No. 10-2008-7005243.
European Search Report mailed Jul. 21, 2011 for the corresponding European patent application No. 06810924.8.

*Primary Examiner* — Peter O Sullivan
(74) *Attorney, Agent, or Firm* — Leason Ellis LLP.

(57) ABSTRACT

This method for producing a potassium perfluoroalkanesulfonate includes an electrochemical fluorination step in which an alkanesulfonyl halide compound is subjected to electrochemical fluorination in anhydrous hydrogen fluoride, thereby to generate a production gas containing perfluoroalkanesulfonyl fluoride as the main component. In addition, for example, the methods may include a gas absorption step in which the production gas is reacted with an aqueous solution of potassium hydroxide, thereby to generate a gas absorbed solution containing potassium perfluoroalkanesulfonate, a purification step in which impurities such as potassium fluoride, potassium hydroxide, and potassium sulfate, are removed, and a concentration and collection step in which the aqueous solution from which the impurities are removed is concentrated and dried. In the electrochemical fluorination, for example, it is possible that the proton concentration in the reaction solution is maintained in the range of 150 to 1,500 ppm to suppress the formation of byproducts.

11 Claims, 2 Drawing Sheets

POTASSIUM PERFLUOROALKANESULFONATE AND METHOD FOR PRODUCING THE SAME

CROSS-REFERENCE TO PRIOR APPLICATION

This is a U.S. National Phase Application under 35 U.S.C. §371 of International Patent Application No. PCT/JP2006/319545 filed Sep. 29, 2006, which claims the benefit of Japanese Patent Application No. 2005-288008 filed Sep. 30, 2005, both of which are incorporated by reference herein. The International Application was published in Japanese on Apr. 5, 2007 as WO 2007/037411 A1 under PCT Article 21(2).

TECHNICAL FIELD

The present invention relates to a potassium perfluoroalkanesulfonate represented by the general formula: $C_nF_{2n+1}SO_3K$, in which n is an integer of 1 to 3, and a method for producing the same, which is suitable as a starting material in the production of a perfluoroalkanesulfonic acid represented by the general formula: $C_nF_{2n+1}SO_3H$, in which n is an integer of 1 to 3, which is useful, for example, as a synthetic catalyst in manufacturing pharmaceuticals.

BACKGROUND ART

As a method for producing a perfluoroalkanesulfonic acid represented by the general formula: $C_nF_{2n+1}SO_3H$, in which n is an integer of 1 to 3, the method described in U.S. Pat. No. 2,732,398 (Patent Document 1) is known. In short, a perfluoroalkanesulfonic acid is produced by a process by which an alkanesulfonyl halide having 1 to 3 carbons is used as the starting material and is subjected to an electrochemical fluorination reaction in hydrogen fluoride, thereby substituting the hydrogens of the alkyl moiety of the alkanesulfonyl halide with fluorine (electrochemical fluorination) to yield a perfluoroalkanesulfonyl fluoride, and the perfluoroalkanesulfonyl fluoride is then reacted with an alkaline solution to convert the perfluoroalkanesulfonyl fluoride into its alkali metal salt, and further the alkali metal salt is subjected to acid decomposition reaction with sulfuric acid.

In the above-mentioned process, however, it is necessary to collect, at low temperatures, the gas of the perfluoroalkanesulfonyl fluoride generated in the electrochemical fluorination step. Furthermore, it is necessary to react the resulting perfluoroalkanesulfonyl fluoride with the alkali at high temperatures and at high pressures. For these reasons, this process has difficulties, for example, in continuous production and is problematic in industrial implementation.

As an improved production method of the process described above, Japanese Unexamined Patent Application, First Publication No. S64-61452 (Patent Document 2) describes a process by which the production gas resulting from electrochemical fluorination is absorbed while converting into a potassium salt, by enhancing the contact between the production gas and an aqueous solution of potassium hydroxide to react the production gas with the aqueous solution at ordinary pressure. This process is characterized in that a potassium perfluoroalkanesulfonate is crystallized from the gas absorbed solution by concentrating the gas absorbed solution or by adding an alkali to the gas absorbed solution, and then is subjected to filtration and the filtrate is recycled in the gas absorption step.

In this process, however, the crystallization of potassium perfluoroalkanesulfonate is carried out under conditions where potassium hydroxide and potassium fluoride, which is yielded as a byproduct in the reaction, are present in their dissolved state in the gas absorbed solution. As a result, potassium perfluoroalkanesulfonate crystals tend to have the potassium hydroxide and potassium fluoride included therein, which are difficult to remove by washing with water after filtration, since they are incorporated into the inside of the crystals. Therefore, it is not easy to reduce the contents of these impurities to a sufficient degree.

For example, in the case where the potassium perfluoroalkanesulfonate contains potassium fluoride in high amounts, hydrogen fluoride is yielded as a byproduct when a perfluoroalkanesulfonic acid is produced by subjecting the potassium perfluoroalkanesulfonate to an acid decomposition reaction, and results in corrosion of reactor materials, such as glass linings, leading to serious industrial problems.

Also, in the case where the potassium perfluoroalkanesulfonate contains potassium hydroxide in high amounts, water is yielded as a byproduct when a perfluoroalkanesulfonic acid is produced by subjecting the potassium perfluoroalkanesulfonate to an acid decomposition reaction by the addition thereto of concentrated sulfuric acid or the like, and results in the formation of a hydrate or hydrates having a high melting point from the water and the perfluoroalkanesulfonic acid, leading to the problem of clogging pipes during the distillation of the perfluoroalkanesulfonic acid under reduced pressure.

Moreover, process steps become complicated, since the filtrate after the filtration of potassium perfluoroalkanesulfonate in this process has large amounts of potassium perfluoroalkanesulfonate which is the target and unreacted potassium hydroxide remaining therein and is required to be recycled and reused in the gas absorption step.

In addition to the above-described methods, there is an alternative method, Japanese Patent No. 3,294,323 (Patent Document 3) which describes a process by which a methanesulfonyl halide is used as the starting material and is subjected to electrochemical fluorination in anhydrous hydrogen fluoride so as to generate trifluoromethanesulfonyl fluoride, and the trifluoromethanesulfonyl fluoride is then washed with water to remove acidic gases, and is reacted with an aqueous solution or slurry of lithium hydroxide to remove lithium fluoride yielded as a byproduct, thereby to produce lithium trifluoromethanesulfonate. The lithium trifluoromethanesulfonate can be subjected to acid decomposition reaction so as to produce a perfluoroalkanesulfonic acid. In this process, however, an aqueous solution of lithium hydroxide is used as an alkaline absorption solution and lithium fluoride which is sparingly soluble in water is formed as a byproduct, resulting in the problem of depositing within and clogging pipes.

In addition, in any of the methods described above, it has been difficult until now in the electrochemical fluorination step to avoid yielding as byproducts fluoroalkanes and sulfonyl difluoride due to decomposition in the electrochemical fluorination reaction. Global warming recently poses problems, and fluoroalkanes yielded by a decomposition reaction, which is a side reaction in the electrochemical fluorination, are a class of greenhouse gases which are key components of global warming and a group of compounds which have highest coefficients among the presently known greenhouse gases, with their warming coefficients being several thousand times that of carbon dioxide. These fluoroalkanes are not absorbed in acidic or alkaline aqueous solutions, making their posttreatments difficult, and therefore reduction of their incidence is required. The previous production technologies described above do not take into account the suppression of the generation of fluoroalkanes as byproducts.

Also, the sulfonyl difluoride yielded as a byproduct in the decomposition reaction forms potassium sulfate when absorbed in an aqueous potassium hydroxide solution, which has a relatively low solubility in water and thus tends to precipitate within the apparatus in the gas absorption step, leading to the problem of clogging pipes. Furthermore, as the decomposition reaction is enhanced, the content of potassium sulfate in the resulting potassium perfluoroalkanesulfonate crystal is increased. In the case where such potassium perfluoroalkanesulfonate is used as the starting material to carry out acid decomposition reaction for synthesizing a perfluoroalkanesulfonic acid, a reaction residue after the distillation of the perfluoroalkanesulfonic acid under reduced pressure solidifies and makes processing difficult.

Patent Document 1 U.S. Pat. No. 2,732,398
Patent Document 2 Japanese Unexamined Patent Application, First Publication No. S64-61452
Patent Document 3 Japanese Patent No. 3,294,323

DISCLOSURE OF THE INVENTION

Problems to be Solved by the Invention

The present invention has solved the above-mentioned problems in the previous methods and provides a potassium perfluoroalkanesulfonate and a method for producing the same which is suitable as a starting material for the industrial production of a perfluoroalkanesulfonic acid.

Specifically, the present invention provides a potassium perfluoroalkanesulfonate which is useful as a starting material in the industrial production of a perfluoroalkanesulfonic acid and has reduced amounts of impurities such as chloride ions, fluoride ions, sulfate ions, and potassium hydroxide, and methods for producing such potassium perfluoroalkanesulfonate which reduce the generation of greenhouse gases resulting from the decomposition reaction in the electrochemical fluorination step, raise no possibility of clogging pipes in the gas absorption step, and provide much more simplified process steps.

Percentages in the following description are mass %, unless otherwise specified.

Means for Solving the Problems

A first aspect of the method for producing potassium perfluoroalkanesulfonate according to the present invention includes: subjecting an alkanesulfonyl halide compound represented by the general formula: $C_nH_{2n+1}SO_2X$, in which n is an integer of 1 to 3 and X is Cl or F, to electrochemical fluorination in anhydrous hydrogen fluoride, thereby to generate a production gas containing, as the main component, perfluoroalkanesulfonyl fluoride represented by the general formula: $C_nF_{2n+1}SO_2F$ in which n is an integer of 1 to 3, (electrochemical fluorination step); reacting the production gas with an aqueous solution of potassium hydroxide, thereby to generate a gas absorbed solution containing potassium perfluoroalkanesulfonate represented by the general formula: $C_nF_{2n+1}SO_3K$, in which n is an integer of 1 to 3, (gas absorption step); removing potassium fluoride, potassium hydroxide, and potassium sulfate which are impurities contained in the gas absorbed solution (purification step); and subjecting the aqueous solution from which the impurities are removed to concentration and drying, thereby to obtain potassium perfluoroalkanesulfonate represented by the general formula: $C_nF_{2n+1}SO_3K$, in which n is an integer of 1 to 3, (concentration and collection step).

In the first aspect described above, an alkanesulfonyl fluoride compound represented by the general formula: $C_nH_{2n+1}SO_2F$ in which n is an integer of 1 to 3, may be used as the starting material for the electrochemical fluorination.

In the electrochemical fluorination step, the decomposition rate of the product, perfluoroalkanesulfonyl fluoride, may be controlled to less than 3% by maintaining the proton concentration in the reaction solution for electrochemical fluorination in the range of 150 to 1,500 ppm.

In the electrochemical fluorination step, the decomposition rate in the electrochemical fluorination reaction may be controlled to less than 3% by retaining a reaction temperature of 0 to 18° C. and a current density of 1 to 3 A/dm$^2$ and maintaining the proton concentration in the reaction solution in the range of 150 to 1,500 ppm.

In the gas absorption step, the gas absorbed solution containing potassium perfluoroalkanesulfonate which has a concentration of potassium hydroxide of less than 1% may be generated.

In the gas absorption step, the gas absorbed solution containing potassium perfluoroalkanesulfonate may be generated by contacting the aqueous solution of potassium hydroxide at a liquid-to-gas ratio of 10 or more relative to the amount of the production gas to be introduced.

In the gas absorption step, an aqueous solution of potassium hydroxide having an initial concentration of potassium hydroxide of 10% or more may be employed, and gas absorption may be carried out until the concentration of potassium hydroxide reaches less than 1%.

In the purification step, alkali metal hydroxide or alkaline earth metal hydroxide may be added to the gas absorbed solution to allow it to react with the potassium fluoride contained in the gas absorbed solution so as to form a fluoride precipitate and potassium hydroxide, and sulfuric acid may be further added to precipitate the potassium hydroxide in the solution as potassium sulfate, and these precipitates may be removed by filtration, and the filtrate may be subjected to concentration and drying to obtain a potassium perfluoroalkanesulfonate.

In the purification step, alkali metal hydroxide or alkaline earth metal hydroxide may be added to the gas absorbed solution to allow it to react with the potassium fluoride contained in the gas absorbed solution so as to form a fluoride precipitate and potassium hydroxide, and perfluoroalkanesulfonic acid may be further added to convert the potassium hydroxide in the solution into potassium perfluoroalkanesulfonate, and the precipitate may be removed by filtration, and in the concentration and collection step, the filtrate may be subjected to concentration and drying to obtain a potassium perfluoroalkanesulfonate.

In the purification step, alkali metal hydroxide or alkaline earth metal hydroxide may be added to the gas absorbed solution to allow it to react with the potassium fluoride contained in the gas absorbed solution so as to form a fluoride precipitate and potassium hydroxide, and a residue of the reaction solution generated in producing perfluoroalkanesulfonic acid by an acid decomposition reaction may be further added to neutralize the potassium hydroxide in the solution, and then the precipitate may be removed by filtration, and in the concentration and collection step, the filtrate may be subjected to concentration and drying to obtain potassium perfluoroalkanesulfonate.

In the purification step, aluminum sulfate may be added to the gas absorbed solution to allow it to react with the potassium fluoride and the potassium hydroxide contained in the gas absorbed solution so as to form a precipitate of fluoride, potassium sulfate, or double salt thereof, and the precipitate may be filtered off, and in the concentration and collection step, the filtrate may be subjected to concentration and drying to obtain potassium perfluoroalkanesulfonate.

A second aspect of the method for producing potassium perfluoroalkanesulfonate according to the present invention includes: subjecting an alkanesulfonyl halide compound represented by the general formula: $C_nH_{2n+1}SO_2X$, in which n is an integer of 1 to 3 and X is Cl or F, to electrochemical fluorination in anhydrous hydrogen fluoride, thereby to generate a gas containing, as the main component, a perfluoroalkanesulfonyl fluoride represented by the general formula: $C_nF_{2n+1}SO_2F$ in which n is an integer of 1 to 3, and employing the production gas to produce a potassium perfluoroalkanesulfonate, wherein in the electrochemical fluorination, the proton concentration in the reaction solution is maintained in the range of 150 to 1,500 ppm to suppress the formation of byproducts.

In the second aspect described above, an alkanesulfonyl fluoride compound represented by the general formula: $C_nH_{2n+1}SO_2F$ in which n is an integer of 1 to 3, may be used as the starting material for the electrochemical fluorination.

In the electrochemical fluorination, the decomposition rate in the electrochemical fluorination reaction may be controlled to less than 3% by maintaining the proton concentration in the reaction solution in the range of 150 to 1,500 ppm.

In the electrochemical fluorination, the decomposition rate in the electrochemical fluorination reaction may be controlled to less than 3% by retaining a reaction temperature of 0 to 18° C. and a current density of 1 to 3 A/dm$^2$, and maintaining the proton concentration in the reaction solution in the range of 150 to 1,500 ppm.

A first aspect of the potassium perfluoroalkanesulfonate according to the present invention is potassium perfluoroalkanesulfonate obtained by the above-mentioned production methods and having a content of chloride ions of less than 50 ppm.

A second aspect of the potassium perfluoroalkanesulfonate according to the present invention is potassium perfluoroalkanesulfonate obtained by the above-mentioned production methods and having a content of fluoride ions of less than 300 ppm.

A third aspect of the potassium perfluoroalkanesulfonate according to the present invention is potassium perfluoroalkanesulfonate obtained by the above-mentioned production methods and having a content of sulfate ions of less than 3%.

A fourth aspect of the potassium perfluoroalkanesulfonate according to the present invention is potassium perfluoroalkanesulfonate obtained by the above-mentioned production methods and having a content of potassium hydroxide of less than 1%.

A fifth aspect of the potassium perfluoroalkanesulfonate according to the present invention is potassium perfluoroalkanesulfonate obtained by the above-mentioned production methods and having a purity of 95% or more.

EFFECTS OF THE INVENTION

In the production methods of the present invention, since the gas yielded in the electrochemical fluorination is allowed to be absorbed in an aqueous solution of potassium hydroxide until the concentration of potassium hydroxide in the gas absorbed solution reaches less than 1% when the gas is absorbed in the aqueous potassium hydroxide solution, alkali concentrations in the gas absorbed solution are sufficiently decreased. Accordingly, recycling and reusing of the gas absorbed solution are not required and process steps are simplified, making the production methods of the present invention industrially favorable.

In the present invention, since electrochemical fluorination is performed while controlling the decomposition rate to less than 3%, the generation of fluoroalkanes and sulfonyl difluoride is extremely low, possibilities of environmental pollution and global warming are reduced, and no clogging of pipes occurs in the gas absorption step.

According to the production methods of the present invention, high-purity potassium perfluoroalkanesulfonate can be obtained which has a purity of 95% or more, and contents of chloride ions of less 50 ppm, fluoride ions of less than 300 ppm, and sulfate ions of less than 3%.

In the case where the potassium perfluoroalkanesulfonate of the present invention is employed as the starting material for producing perfluoroalkanesulfonic acid, since the content of fluoride ions is sufficiently decreased, hydrogen fluoride is generated as a byproduct in smaller amounts and no corrosion of apparatus materials such as glass linings occurs. Also, because of the low content of potassium hydroxide, there is not raised the possibility that perfluoroalkanesulfonic acid forms a hydrate or hydrates and clogging of pipes occurs. In addition, because of the low content of potassium sulfate, a reaction solution after the distillation of the product does not solidify, allowing one to carry out processing with ease.

BRIEF DESCRIPTION OF THE REFERENCED NUMERALS

Figure 1:
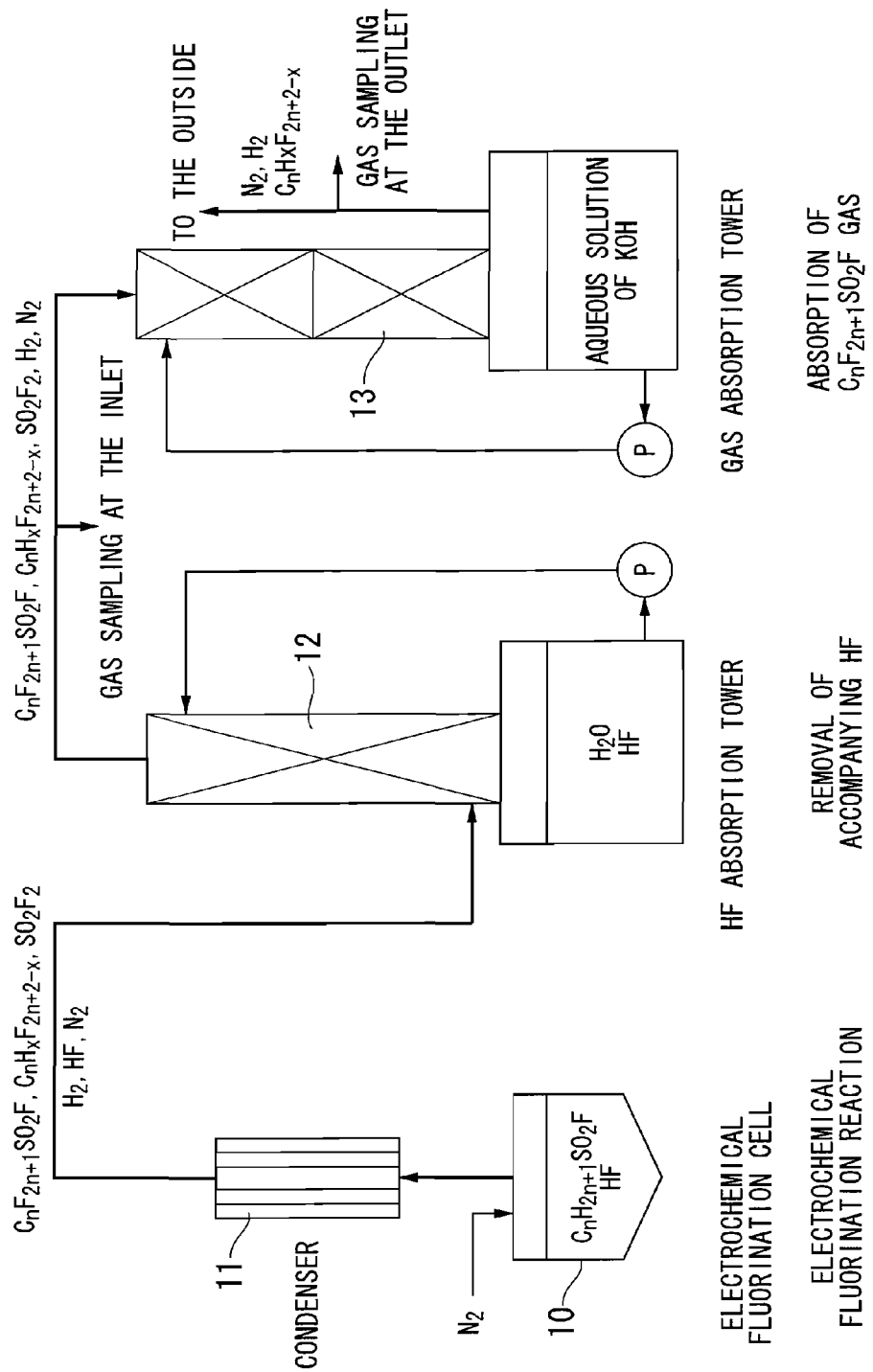
FIG. 1 is a process chart of the steps of electrochemical fluorination and gas absorption.

10 Electrochemical fluorination cell
11 Condenser
12 HF absorption tower
13 Gas absorption tower
20 Stirring tank
21 Filter
22 Concentrator/drier
23 Condenser
24 Water collecting vessel

BEST MODE FOR CARRYING OUT THE INVENTION

The organization of the present invention is now explained with reference to the drawings.

[Starting Material]

In production methods of the present embodiments, alkanesulfonyl halide compounds represented by the general formula $C_nH_{2n+1}SO_2X$, in which n is an integer of 1 to 3 and X is Cl or F can be used as the starting material for electrochemical fluorination. Especially when alkanesulfonyl fluoride is employed, the content of chloride ions in the finally obtained potassium perfluoroalkanesulfonate can be reduced to less than 50 ppm, which makes the production methods of the present invention more preferable. On the other hand, in the case where alkanesulfonyl chloride is used as the starting material for electrochemical fluorination, the content of chloride ions in the finally obtained potassium perfluoroalkanesulfonate is increased, and leads to the tendency to cause mixing of chloride ions into the final desired product and the possibility of reducing quality is raised, when such potassium perfluoroalkanesulfonate is subjected to acid decomposition to produce perfluoroalkanesulfonic acid. Alkanesulfonyl fluoride can be easily produced by subjecting alkanesulfonyl chloride to fluorine displacement while employing potassium fluoride or the like, as shown in the following formula:

$$C_nH_{2n+1}SO_2Cl + KF \rightarrow C_nH_{2n+1}SO_2F + KCl$$

[Electrochemical Fluorination Step]

It is recommendable that as the starting material, alkanesulfonyl halide, preferably alkanesulfonyl fluoride, is employed and charged into an electrochemical fluorination cell with hydrogen fluoride to carry out electrochemical fluorination under an atmosphere of a nitrogen gas at ordinary pressure. In the electrochemical fluorination step, the alkyl moiety of alkanesulfonyl halide represented by the general formula $C_nH_{2n+1}SO_2X$, in which n is an integer of 1 to 3 and X is Cl or F, is substituted with fluorine to generate perfluoroalkanesulfonyl fluoride represented by the general formula $C_nF_{2n+1}SO_2F$, in which n is an integer of 1 to 3, as shown in the formula described below. As side reactions, decomposing of the starting material, intermediates, and the produced $C_nF_{2n+1}SO_2F$ causes the generation of fluoroalkanes, such as tetrafluoromethane ($CF_4$), and sulfonyl difluoride ($SO_2F_2$).

Main Reaction: $C_nH_{2n+1}SO_2F + (2n+1)HF \rightarrow C_nF_{2n+1}SO_2F\uparrow + (2n+1)H_2\uparrow$ Side Reaction: $C_nH_{2n+1}SO_2F + HF \rightarrow C_nH_xF_{2n+2-x}$, $SO_2F_2$, and the like in which n is an integer of 1 to 3 and x is an integer of 0 to 2n+2.

Each perfluoroalkanesulfonyl fluoride thus produced has a low boiling point of, for example, −21° C. (n=1), 0° C. (n=2), and 40° C. (n=3), and thus is discharged as gas from the electrochemical fluorination cell to the outside along with hydrogen generated as a byproduct, decomposed products such as fluoroalkanes and sulfonyl difluoride, the substitution gas of nitrogen, and the electrochemical fluorination solvent of hydrogen fluoride.

In the above-mentioned electrochemical fluorination, it is preferable to perform the electrochemical fluorination while maintaining the proton concentration in the reaction solution in the range of 150 to 1,500 ppm. By maintaining the proton concentration in the reaction solution in the range of 150 to 1,500 ppm, it is possible to control the decomposition rate in the electrochemical fluorination reaction to less than 3% and to reduce the formation of byproducts.

The proton concentration in the reaction solution is a value indicating the mass concentration of protons (hydrogens) which are possessed by the starting material and intermediates (compounds in which one or more hydrogens of their alkyl moiety remain) in the reaction solution, and can be determined by conducting a nuclear magnetic resonance analysis ($^1$H-NMR) of the reaction solution employing an internal standard.

The decomposition rate refers to the incidence of a decomposition reaction or reactions which is/are a side reaction in the electrochemical fluorination. Specifically, the decomposition rate is expressed by the ratio of the formed amount of a byproduct, sulfonyl difluoride ($SO_2F_2$) to the sum of the formed amounts of the main product, perfluoroalkanesulfonyl fluoride and of a byproduct, sulfonyl difluoride. These amounts can be given, for example, by the peak area for each of these components on a chromatogram in gas-chromatography analysis of an electrochemical fluorination production gas.

Decomposition rate (%)=[formed amount of $SO_2F_2$]/
 ([formed amount of $C_nF_{2n+1}SO_2F$]+[formed
 amount of $SO_2F_2$])×100

In which each of these amounts is given by its peak area in gas-chromatography analysis.

The present inventors have found that there is a correlation between the proton concentration and the decomposition rate and that it is possible to control the decomposition rate to less than 3% by maintaining the proton concentration in the reaction solution in the range of 150 to 1,500 ppm in the reaction temperature range of 0° C. to 18° C. and the current density range of 1 to 3 A/dm².

By controlling the decomposition rate to less than 3%, the generation of fluoroalkanes can be reduced and contribution can be made to the prevention of warming. In addition, at the same time, since the generation of sulfonyl difluoride is reduced, the generation of potassium sulfate as a byproduct, which is yielded by the reaction of the sulfonyl difluoride with potassium hydroxide in the gas absorption step, can be suppressed.

[Gas Absorption Step]

The production gas discharged from the electrochemical fluorination cell in the electrochemical fluorination step is passed through a condenser at 0 to −40° C.; thereby, the accompanying hydrogen fluoride is liquefied, and is returned into the electrochemical fluorination cell. Since the production gas discharged from the outlet of the condenser contains hydrogen fluoride that has not been liquefied in the condenser, the production gas is preferably washed by gas-liquid contacting with a shower of water or a low-concentration aqueous alkaline solution so as to remove the hydrogen fluoride, and then directed to a gas absorption tower where the production gas is contacted with an alkaline solution. As the alkaline solution, an aqueous solution of potassium hydroxide is employed, and gas-liquid contact is made between the production gas described above and the aqueous potassium hydroxide solution, so that the perfluoroalkanesulfonyl fluoride contained in the production gas is absorbed in the aqueous potassium hydroxide solution.

In the gas absorption step, as shown in the formula described below, perfluoroalkanesulfonyl fluoride, which is the main component contained in the electrochemical fluorination production gas, is reacted with the potassium hydroxide and forms a potassium perfluoroalkanesulfonate, which is dissolved and absorbed in the solution. On the other hand, fluoroalkanes, which are byproducts contained in the electrochemical fluorination production gas, are not absorbed in the aqueous potassium hydroxide solution and thus discharged to the outside. In addition, sulfonyl difluoride ($SO_2F_2$), which is a byproduct also contained in the electrochemical fluorination production gas, is absorbed in the aqueous potassium hydroxide solution and yields potassium sulfate and potassium fluoride.

Main Reaction: $C_nF_{2n+1}SO_2F + 2KOH \rightarrow C_nF_{2n+1}SO_3K + KF + H_2O$ Side Reaction: $SO_2F_2 + 4KOH \rightarrow K_2SO_4\downarrow + 2KF + 2H_2O$ In the case of high decomposition rates in the electrochemical fluorination step, there are generated large amounts of sulfonyl difluoride as a byproduct, and the sulfonyl difluoride is reacted with the potassium hydroxide in the gas absorbed solution and it results in the formation of large amounts of potassium sulfate. This leads to the consumption of large amounts of the potassium hydroxide, as well as an increase in the content of potassium sulfate in potassium perfluoroalkanesulfonate crystals. Furthermore, potassium sulfate has a relatively low solubility in water (7.35 g/100 g (0° C.) and 24.1 g/100 g (100° C.)), and also has a further decreased solubility and tends to precipitate by virtue of the salting-out effect when potassium perfluoroalkanesulfonate coexists in a solution. Consequently, the problem is brought about that when the amount of potassium sulfate in the gas absorbed solution is increased, clogging of pipes through which the solution is circulated in the gas absorption step is caused by the precipitation of the potassium sulfate.

In the gas absorption step, it is recommendable that an aqueous solution of potassium hydroxide having a concentration of 10% or more is employed and the production gas is allowed to be absorbed by the same until the concentration of potassium hydroxide reaches less than 1%. In this case, it is recommendable to keep the temperature of the aqueous potassium hydroxide solution (absorption solution) at 40 to 90° C., preferably 50 to 80° C., and to adjust the flow rate of circulation and to make gas-liquid contact such that the liquid-to-gas ratio of the amounts of the aqueous potassium hydroxide solution and the production gas to be introduced is 10 or more. By controlling the liquid-to-gas ratio to 10 or more in the temperature range described above, gas absorption can be continued while maintaining the gas absorption rate between 95 and 100%, until the concentration of potassium hydroxide reaches less than 1%.

In the case where the absorption step is started at a potassium hydroxide concentration of 10% or more and is continued until the concentration of potassium hydroxide reaches less than 1%, the concentration of potassium perfluoroalkanesulfonate in the gas absorbed solution is increased and a content of potassium sulfate can be decreased by the salting-out effect thereof, which makes the production methods of the present invention advantageous. Even in the case of employing an aqueous potassium hydroxide solution with such a high concentration, it is possible to prevent clogging of pipes due to precipitation of potassium sulfate, if the decomposition rate in the electrochemical fluorination reaction is controlled to less than 3%. However, when the concentration of potassium hydroxide is 40% or more, the viscosity of the aqueous solution is increased, leading to difficulties in handling. Therefore, it is appropriate that the concentration of the aqueous potassium hydroxide solution is between 10 and 40%.

The gas absorption rate is given by the formula described below, in which the amounts of the perfluoroalkanesulfonyl fluoride ($C_nF_{2n+1}SO_2F$) and $N_2$ are given by their peak areas on a chromatogram in gas-chromatography analysis of gases from the inlet and the outlet of the gas absorption tower.

Gas absorption rate (%)=[1−($C_nF_{2n+1}SO_2F$ mass ratio)×($N_2$ mass ratio)]×100 in which, $C_nF_{2n+1}SO_2F$ mass ratio=$C_nF_{2n+1}SO_2F$ amount at the outlet/$C_nF_{2n+1}SO_2F$ amount at the inlet, and
$N_2$ mass ratio=$N_2$ amount at the inlet/$N_2$ amount at the outlet.

[Purification Step]

The purification step is a step in which potassium fluoride, which is yielded as a byproduct in the main reaction in the above-mentioned absorption step, potassium sulfate and potassium fluoride, which are yielded in the side reactions, and potassium hydroxide, which has not been consumed in the gas absorption step, are removed. As methods thereof, there are: (A) a method by which the gas absorbed solution is treated with an alkali metal hydroxide or alkaline earth metal hydroxide, and then is neutralization with an acid, and (B) a method by which the gas absorbed solution is treated with aluminum sulfate.

(A) The method in which alkali metal hydroxide or alkaline earth metal hydroxide is employed has a first step of adding any of these hydroxides to the above-described gas absorbed solution to form a sparingly insoluble fluoride precipitate and potassium hydroxide by the reaction with the potassium fluoride dissolved in the gas absorbed solution (1st step) and a second step of subsequently adding sulfuric acid, either after filtering the precipitate once or without filtration, to react with the dissolved potassium hydroxide to form a potassium sulfate precipitate (2nd step), and then the precipitate(s) is filtrated.

As an example of alkali metal hydroxides or alkaline earth metal hydroxides, calcium hydroxide is suitable. Calcium hydroxide is added to the gas absorbed solution to form a precipitate of calcium fluoride (1st step), and sulfuric acid is further added to form a precipitate of potassium sulfate (2nd step), and then these precipitates are filtrated. Filtration may be performed separately in each of the 1st and 2nd steps.

1st step: $2KF+Ca(OH)_2 \rightarrow CaF_2\downarrow +2KOH$

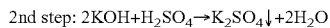

2nd step: $2KOH+H_2SO_4 \rightarrow K_2SO_4\downarrow +2H_2O$

In the 1st step, lithium hydroxide may be employed instead of calcium hydroxide. In this case, a precipitate of lithium fluoride is formed, as shown in the formula described below, and has better filterability than the above-described calcium fluoride precipitate, resulting in easy filtration. On the other hand, since calcium fluoride has a lower solubility in water than that of lithium fluoride, calcium fluoride has the advantage that the amount of fluoride ions can be reduced to a lower level.

1st step: $KF+LiOH \rightarrow LiF\downarrow +KOH$

The alkali metal hydroxide or alkaline earth metal hydroxide is added at a molar ratio of 0.5 to 2.5, preferably 0.5 to 1.0, relative to the potassium fluoride dissolved in the gas absorbed solution, and the mixture is heated to a temperature of 50 to 90° C. and is stirred for 1 to 4 hours, to allow precipitation of the potassium fluoride in the solution. In this case, the dissolved fluoride ions in the gas absorbed solution, which are present in an amount of more than 10,000 ppm, can be decreased to a great extent, so that the fluoride ions can be decreased to less than 300 ppm as the content of fluoride ion in a potassium perfluoroalkanesulfonate crystal.

It is recommendable in the 2nd step that sulfuric acid having a concentration of 50 to 100% is added slowly to the solution which has been treated in the 1st step, with heating to 20 to 90° C. and stirring, and the addition of sulfuric acid is stopped when the pH becomes neutral, and then stirring is continued for another 1 to 4 hours.

In the 2nd step, a perfluoroalkanesulfonic acid may be employed instead of sulfuric acid. In this case, as shown in the formula described below, the potassium hydroxide in the solution is reacted with the perfluoroalkanesulfonic acid and forms a potassium perfluoroalkanesulfonate. Consequently, the content of potassium sulfate is decreased to an extremely low degree, compared with the neutralization with sulfuric acid, and a high-purity potassium perfluoroalkanesulfonate having a content of sulfate ions of less than 1% can be provided by concentration and drying.

2nd step: $KOH+C_nF_{2n+1}SO_3H \rightarrow C_nF_{2n+1}SO_3K+H_2O$

Furthermore, as the acid which can be used for neutralization in the 2nd step, one may use a reaction residue which is obtained after adding sulfuric acid to the potassium perfluoroalkanesulfonate to carry out acid decomposition to form perfluoroalkanesulfonic acid and removing the perfluoroalkanesulfonic acid by distillation. This residue contains perfluoroalkanesulfonic acid which has not been removed by distillation and potassium sulfate which is a reaction byproduct, as well as sulfuric acid which is used in excess in the acid decomposition reaction, and thus the sulfuric acid and the perfluoroalkanesulfonic acid which are usually discarded can be used effectively, which makes the production methods of the present invention preferable.

In addition, in the 2nd step, by removing the potassium sulfate in the gas absorbed solution as much as possible, the amount of sulfate ions can be reduced which is contained in a potassium perfluoroalkanesulfonate crystal derived from the gas absorbed solution. In order to do so, it is effective that, as has been already described above, for example, the concentration of potassium perfluoroalkanesulfonate in the gas absorbed solution is increased so as to precipitate potassium sulfate through the salting-out effect thereof.

In order to increase the concentration of potassium perfluoroalkanesulfonate in the gas absorbed solution, it is preferable, as has been already mentioned, that in the gas absorption step, the initial concentration of an aqueous potassium hydroxide solution which is used as the absorption solution is 10% or more and the concentration of potassium hydroxide at the end is less than 1%, and additionally the decomposition rate in the electrochemical fluorination reaction is 3% or less. Consequently, the concentration of potassium perfluoroalkanesulfonate in the gas absorbed solution in the 2nd step of purification is increased, so that the content of sulfate ions in a potassium perfluoroalkanesulfonate crystal can be reduced to less than 3%.

In the gas absorption step, when the gas absorption is carry out at an initial concentration of potassium hydroxide of less than 10%, the concentration of potassium perfluoroalkanesulfonate in the gas absorbed solution is decreased and the salting-out effect is attenuated. Therefore, a concentration of potassium sulfate becomes relatively high. In this case, it is possible to decrease the potassium sulfate by concentrating the gas absorbed solution in the 2nd step of purification to increase the concentration of potassium perfluoroalkanesulfonate, but this method is unpreferable, because of diminishing productivity and increasing process steps.

In the case of employing potassium perfluoroalkanesulfonate with a sulfate ion content of less than 3%, a reaction solution does not solidify after the product is distilled following the reaction, without the use of sulfuric acid in a large excess in the production of perfluoroalkanesulfonic acid by an acid decomposition reaction, allowing one to carry out processing with ease.

(B) In the purification method employing aluminum sulfate, the potassium fluoride and potassium hydroxide dissolved in the gas absorbed solution react with aluminum sulfate, and aluminum fluoride, potassium sulfate, or a double salt thereof is formed and precipitates. Therefore, these salts should be filtered out.

It is recommendable that aluminum sulfate is added at a molar ratio of 0.1 to 1.0, preferably 0.1 to 0.3, relative to the sum of the amounts of the potassium fluoride and potassium hydroxide dissolved in the gas absorbed solution, the mixture is heated to 50 to 90° C. and stirred for 1 to 4 hours, and then cooled to 0 to 10° C. with leaving the mixture to stand for 1 to 10 hours.

This method can decrease the dissolved fluoride ions in the gas absorbed solution to a great degree as in Method (A), so that it is possible to reduce the content of fluoride ions in a potassium perfluoroalkanesulfonate crystal to less than 300 ppm. In addition, since this treatment does not give any alkali as a byproduct, this treatment does not require a neutralization step in which an acid is used [the 2nd step in Method (A)], which also makes it possible to simplify the process steps.

[Concentration and Collection Step]

One can collect a potassium perfluoroalkanesulfonate crystal having a purity of 95% or more by concentrating and drying a solution containing potassium perfluoroalkanesulfonate in which the amounts of fluoride ions, sulfate ions, and potassium hydroxide, have been reduced by the production steps described above.

For concentration and drying of the solution, procedures which are usually employed are applicable. Methods by which concentration and drying are carried out under reduced pressure with stirring are particularly preferable. In such methods, the obtained crystal of potassium perfluoroalkanesulfonate has a low content of water, is a fine powder, and results in easy handling.

[Acid Decomposition Step]

A perfluoroalkanesulfonic acid can be produced by adding sulfuric acid to potassium perfluoroalkanesulfonate for acid decomposition to take place, as shown in the formula described below. The reaction is usually performed under ordinary pressure at a temperature of 100 to 180° C. with stirring for 1 to 20 hours by the addition of sulfuric acid at a molar ratio of 1 to 10, preferably 2 to 5, relative to the potassium perfluoroalkanesulfonate. After the reaction is completed, the resulting perfluoroalkanesulfonic acid is distilled under reduced pressure; thereby, the desired product can be obtained.

Main Reaction: $2C_nF_{2n+1}SO_3K + H_2SO_4 \rightarrow 2C_nF_{2n+1}SO_3H + K_2SO_4$

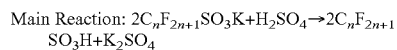

In the acid decomposition step, in the case where the potassium perfluoroalkanesulfonate which is used as the starting material has a high content of fluoride ions, hydrogen fluoride is yielded in a large amount, as shown in the side reaction described below, and corrodes apparatus materials such as glass linings. Also, in the case where the content of potassium hydroxide is high, the potassium hydroxide reacts with sulfuric acid and yields water, and further water forms a solvate or solvates with perfluoroalkanesulfonic acid. The solvate(s) have a high melting point and raise(s) the possibility of clogging pipes during the distillation of the desired product under reduced pressure. Furthermore, in the case where the starting material has a high content of potassium sulfate, the reaction solution solidifies after the product is distilled following the acid decomposition reaction, which makes the treatment thereof difficult.

Side Reaction: $2KF + H_2SO_4 \rightarrow 2HF + K_2SO_4$

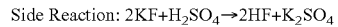

The flow of the production methods described above is shown in FIGS. 1 and 2, although the production process according to the present invention is not limited to the illustrated embodiments. FIG. 1 shows the steps of electrochemical fluorination and gas absorption. An alkanesulfonyl fluoride ($C_nH_{2n+1}SO_2F$) and hydrogen fluoride are placed into the electrochemical fluorination cell 10, a nitrogen atmosphere is provided, and electrochemical fluorination is carried out during which the reaction temperature is controlled to 0 to 18° C., the proton concentration in the reaction solution is controlled to 150 to 1,500 ppm, and the decomposition rate is maintained to less than 3%. The production gas is directed through a condenser 11 to an HF absorption tower 12 to make gas-liquid contact with water or a low-concentration aqueous alkaline solution. Water or a low-concentration aqueous alkaline solution is sparged from the top of the HF absorption tower 12 and the production gas is washed. The washed production gas is directed to a gas absorption tower 13. An aqueous solution of potassium hydroxide is sparged from the top of the gas absorption tower 13 and the main product in the production gas reacts with the potassium hydroxide by gas-liquid contacting and yields potassium perfluoroalkanesulfonate ($C_nF_{2n+1}SO_3K$), which is absorbed in the aqueous potassium hydroxide solution. On the other hand, fluoroalkanes, nitrogen gas, and hydrogen gas which accompany the production gas are not absorbed in the aqueous potassium hydroxide solution and discharged to the outside.

Figure 2:
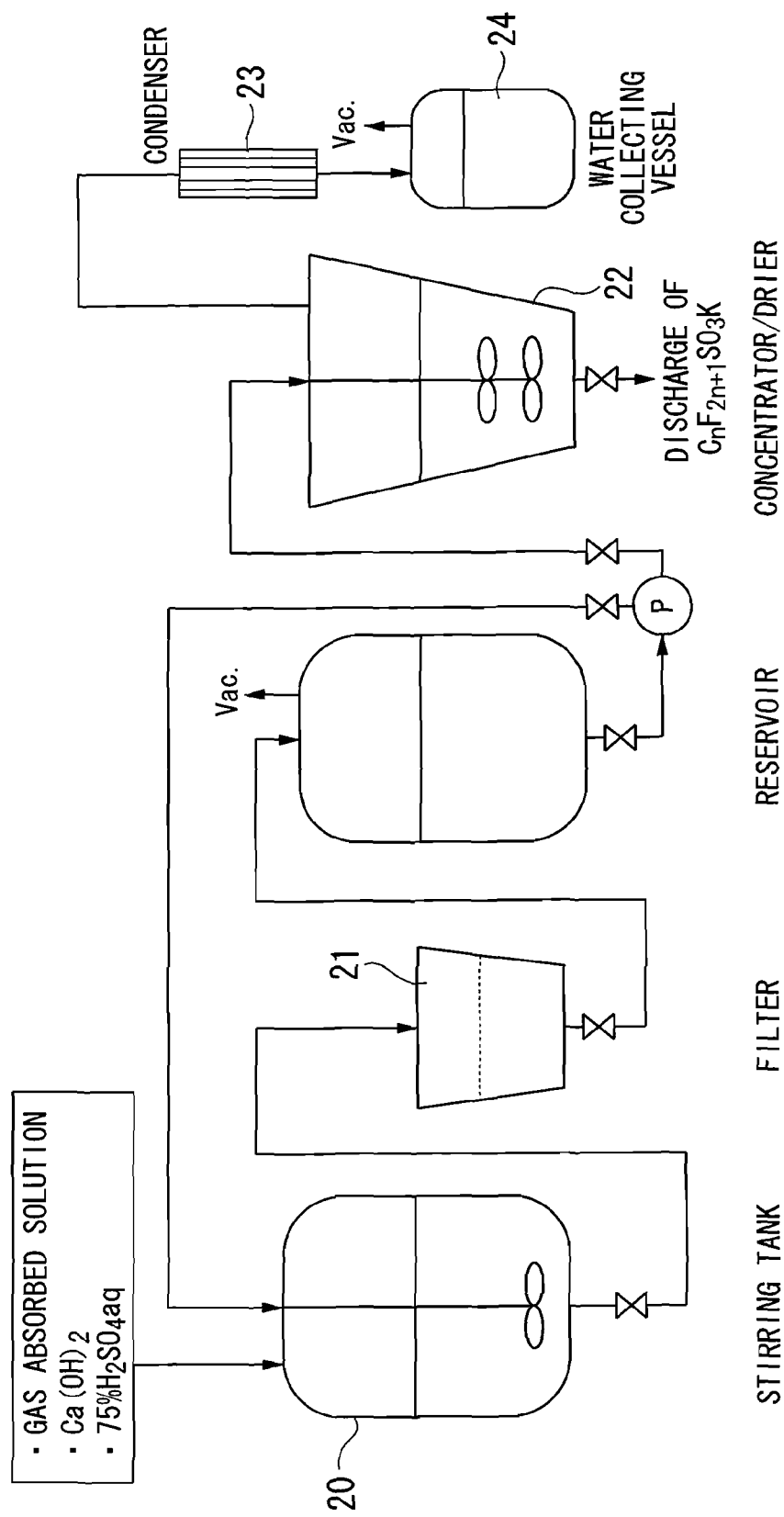
FIG. 2 is a process chart of the steps of purification, and concentration and collection.

FIG. 2 shows the process steps of purification, concentration and drying of the gas absorbed solution containing potassium perfluoroalkanesulfonate ($C_nF_{2n+1}SO_3K$), and collection of the potassium perfluoroalkanesulfonate. In a stirring tank 20, the gas absorbed solution is treated with calcium hydroxide. After the treatment, a liquid containing a precipitate is directed to a filter 21, the solid and liquid are separated, and then the filtrate is returned to the stirring tank 20. Subsequently, sulfuric acid is added for treatment. After the treatment, a liquid containing a precipitate is directed to the filter 21, the solid and liquid are separated, after which the filtrate is directed to a concentrator and dryer 22, and a perfluoroalkanesulfonic acid crystal concentrated by heating and drying under reduced pressure is discharged from the bottom. Evaporated water and others are directed through a condenser 23 to a water collecting vessel 24.

EXAMPLES

Examples of the present invention will be illustrated below.

Example 1

An iron electrochemical fluorination cell equipped with a reflux condenser set to −30° C. was employed and nickel electrodes having a surface area of 378 dm$^2$ for each of the anode and the cathode were placed within the electrochemical fluorination cell. The electrochemical fluorination cell was charged with anhydrous hydrogen fluoride (84.8 kg, 4,240 mol) and the starting material, methanesulfonyl fluoride (1.73 kg, 17.6 mol), such that the proton concentration in a reaction solution was about 600 ppm, and the solution was circulated to prepare the reaction solution.

Electrochemical fluorination was performed at a constant current of 800 A while keeping the temperature to 8 to 12° C. by circulating the reaction solution through an external cooler. During the electrochemical fluorination, methanesulfonyl fluoride and anhydrous hydrogen fluoride, as required, were supplied into the electrochemical fluorination cell to supplement the reaction solution, so that the proton concentration in the reaction solution was maintained in the range of 150 to 1,500 ppm.

The production gas containing trifluoromethanesulfonyl fluoride generated by the electrochemical fluorination was introduced into an HF absorption tower. In the HF absorption tower, ion-exchanged water was circulated at room temperature and subjected to countercurrent contacting with the production gas to remove the accompanying hydrogen fluoride.

Subsequently, the production gas from which the hydrogen fluoride had been removed was introduced into a gas absorption tower. The gas absorption tower had been charged in advance with 214 kg of a 24% aqueous solution of potassium hydroxide and the aqueous potassium hydroxide solution was circulated at a rate of 11 m$^3$/h within the gas absorption tower while adjusting the temperature of the aqueous solution to 60° C. so as to allow the reaction between trifluoromethanesulfonyl fluoride and potassium hydroxide to take place.

When the current was stopped after 92.5 hours had passed from the beginning of the electrochemical fluorination, 268 kg of the reaction solution (hereinafter referred to as gas absorbed solution) within the gas absorption tower was collected. This solution was a colorless and clear solution. Titration analysis of this solution showed that the concentration of potassium hydroxide was 0.9%.

In this fluorination, the proton concentration in the reaction solution within the electrochemical fluorination cell changed between 400 and 800 ppm, the total amount of the starting material fed in the electrochemical fluorination reaction was 41.4 kg (422.0 mol), the voltage changed between 5.5 and 5.7 V, the decomposition rate was 1.8% or less, the liquid-to-gas ratio in the gas absorption reaction was 12.7, and the gas absorption rate was 96% or more.

Example 2

The gas absorbed solution produced in Example 1 was placed into a fluorocarbon resin (PTFE)-lining reaction vessel. 26.2 kg (353.7 mol) of calcium hydroxide powder was added to this gas absorbed solution, and the mixture was heated to 70° C. with stirring.

After the temperature rose, stirring was continued for 2 hours to convert the dissolved potassium fluoride to calcium fluoride. Two hours later, stirring was stopped and the mixture was left to stand overnight, allowing the calcium fluoride to settle. After this aqueous solution was decanted, the calcium fluoride was removed by filtration.

75% sulfuric acid was added to the resulting filtrate until the pH reached the range of 7.0 to 7.5 (the amount of addition: 27.8 kg (212.3 mol)) and neutralization was conducted with stirring. When doing so, the temperature of the solution rose to 70° C. due to heat generation through the neutralization. Stirring was continued for 1 hour in order to complete the neutralization reaction. One hour later, stirring was stopped, and the formed potassium sulfate was allowed to settle by standing. The potassium sulfate was removed by filtration.

The colorless and clear aqueous solution of potassium trifluoromethanesulfonate (219 kg) obtained by this filtration was subjected to concentration and drying to give 53.6 kg of potassium trifluoromethanesulfonate. Ion-chromatography analysis of the product showed that the purity of potassium trifluoromethanesulfonate was 97.2%, the content of sulfate ions was 1.5%, the content of fluoride ions was 120 ppm, the content of chloride ions was 16 ppm, and no potassium hydroxide was detected.

Example 3

Instead of adding a calcium hydroxide powder to the gas absorbed solution in Example 2, aluminum sulfate (21.8 kg, 63.7 mol) was added to the gas absorbed solution (267 kg) and the mixture was heated to 70° C. with stirring.

After the temperature rose, stirring was continued for 2 hours, after which stirring was stopped and the mixture was left to stand at 5° C. overnight to settle the solid. After this aqueous solution was decanted, the precipitate was removed by filtration.

The colorless and clear aqueous solution of potassium trifluoromethanesulfonate (225 kg) obtained by this filtration was subjected to concentration and drying to give 51.1 kg of potassium trifluoromethanesulfonate. Analysis of the product showed that the purity of potassium trifluoromethanesulfonate was 95.9%, the content of sulfate ions was 2.3%, the content of fluoride ions was 246 ppm, the content of chloride ions was 12 ppm, and no potassium hydroxide was detected.

Example 4

Instead of adding 75% sulfuric acid to the filtrate from which the calcium fluoride had been removed by filtration in Example 2, trifluoromethanesulfonic acid was added (the amount of addition: 63.8 kg) until the pH reached the range of 7.0 to 7.5 and neutralization was conducted. Stirring was continued for 1 hour in order to complete the neutralization reaction. One hour later, stirring was stopped and the insoluble material was removed by filtration.

The colorless and clear aqueous solution of potassium trifluoromethanesulfonate (219 kg) obtained by this filtration was subjected to concentration and drying to give 119.8 kg of potassium trifluoromethanesulfonate. Analysis of the product showed that the purity of potassium trifluoromethanesulfonate was 98.5%, the content of sulfate ions was 0.8%, the content of fluoride ions was 180 ppm, the content of chloride ions was 16 ppm, and no potassium hydroxide was detected.

COMPARATIVE EXAMPLES

Comparative Examples 1 to 3

The electrochemical fluorination in Example 1 was carried out by keeping the proton concentration in the reaction solution in the range of 9,000 to 11,200 ppm (Comparative Example 1), 5,000 to 7,050 ppm (Comparative Example 2), and 3,400 to 4,650 ppm (Comparative Example 3). The decomposition rates for these Comparative Examples were 11.3 to 15.5%, 8.3 to 12.0%, and 6.8 to 7.6%, respectively, and tetrafluoromethane and sulfonyl difluoride as byproducts were yielded in large amounts.

Example 5

An iron electrochemical fluorination cell equipped with a reflux condenser set to −20° C. was employed and nickel electrodes having a surface area of 67 dm$^2$ for each of the anode and the cathode were placed within the electrochemical fluorination cell. The electrochemical fluorination cell was charged with anhydrous hydrogen fluoride (11.81 kg, 590 mol) and the starting material, ethanesulfonyl fluoride (0.24 kg, 2.1 mol), such that the proton concentration in the reaction solution was about 600 ppm, and the solution was circulated to prepare the reaction solution.

Electrochemical fluorination was performed at a constant current of 100 A while keeping the temperature to 8 to 12° C. by circulating the reaction solution through an external cooler. During the electrochemical fluorination, ethanesulfonyl fluoride and anhydrous hydrogen fluoride, as required, were supplied into the electrochemical fluorination cell to supplement the reaction solution, so that the proton concentration in the reaction solution was maintained in the range of 150 to 1,500 ppm.

The production gas containing perfluoroethanesulfonyl fluoride generated by the electrochemical fluorination was introduced into an HF absorption tower. In the HF absorption tower, ion-exchanged water was circulated at room temperature and subjected to countercurrent contacting with the production gas to remove the accompanying hydrogen fluoride.

Subsequently, the production gas from which the hydrogen fluoride had been removed was introduced into a gas absorption tower. The gas absorption tower had been charged in advance with 48.0 kg of a 20% aqueous solution of potassium hydroxide and the aqueous potassium hydroxide solution was circulated at a rate of 2 m$^3$/h within the gas absorption tower while adjusting the temperature of the aqueous solution to 60° C. so as to allow the reaction between perfluoroethanesulfonyl fluoride and potassium hydroxide to take place.

When the current was stopped after 300 hours had passed from the beginning of the electrochemical fluorination, 58.9 kg of the reaction solution (gas absorbed solution) within the gas absorption tower was collected. This solution was a colorless and clear solution. Titration analysis of this solution showed that the concentration of potassium hydroxide was 0.2%.

In this fluorination, the proton concentration in the reaction solution changed between 550 and 780 ppm, the total amount of the starting material fed in the electrochemical fluorination reaction was 13.4 kg (119.5 mol), the voltage changed between 5.1 and 5.4 V, the decomposition rate was 2.7% or less, the liquid-to-gas ratio in the gas absorption reaction was 27.0, and the gas absorption rate was 96% or more.

Example 6

The gas absorbed solution produced in Example 5 was placed into a fluorocarbon resin (PTFE)-lining reaction vessel. 5.15 kg (69.6 mol) of a calcium hydroxide powder was added to this gas absorbed solution, and the mixture was heated to 70° C. with stirring.

After the temperature rose, stirring was continued for 2 hours, after which stirring was stopped and the mixture was left to stand overnight, allowing the solid to settle. After this aqueous solution was decanted, the calcium fluoride was removed by filtration.

75% sulfuric acid was added to the resulting filtrate until the pH reached the range of 7.0 to 7.5 (the amount of addition: 4.86 kg (37.2 mol)) and neutralization was conducted with stirring. Stirring was continued for 1 hour in order to complete the neutralization reaction. One hour later, stirring was stopped and the formed potassium sulfate was allowed to settle by standing. The potassium sulfate was removed by filtration.

The obtained colorless and clear aqueous solution of potassium perfluoroethanesulfonate (45.6 kg) was subjected to concentration and drying to give 14.3 kg of potassium perfluoroethanesulfonate. Ion-chromatography analysis of the product showed that the purity of potassium perfluoroethanesulfonate was 96.2%, the content of sulfate ions was 2.1%, the content of fluoride ions was 240 ppm, the content of chloride ions was 25 ppm, and no potassium hydroxide was detected.

Example 7

An iron electrochemical fluorination cell equipped with a reflux condenser set to −20° C. was employed and nickel electrodes having a surface area of 67 dm$^2$ for each of the anode and the cathode were placed within the electrochemical fluorination cell. The electrochemical fluorination cell was charged with anhydrous hydrogen fluoride (11.81 kg, 590 mol) and the starting material, 1-propanesulfonyl fluoride (0.24 kg, 1.90 mol), such that the proton concentration in the reaction solution was about 600 ppm, and the solution was circulated to prepare the reaction solution.

Electrochemical fluorination was performed at a constant current of 100 A while keeping the temperature to 8 to 12° C. by circulating the reaction solution through an external cooler. During the electrochemical fluorination, 1-propanesulfonyl fluoride and anhydrous hydrogen fluoride, as required, were supplied into the electrochemical fluorination cell to supplement the reaction solution, so that the proton concentration in the reaction solution was maintained in the range of 150 to 1,500 ppm.

The production gas containing 1-perfluoropropanesulfonyl fluoride generated by the electrochemical fluorination was introduced into an HF absorption tower. In the HF absorption tower, ion-exchanged water was circulated at room temperature and subjected to countercurrent contacting with the production gas to remove the accompanying hydrogen fluoride.

Subsequently, the production gas from which the hydrogen fluoride had been removed was introduced into a gas absorption tower. The gas absorption tower had been charged in advance with 48.0 kg of a 20% aqueous solution of potassium hydroxide and the aqueous potassium hydroxide solution was circulated at a rate of 2 m³/h within the gas absorption tower while adjusting the temperature of the aqueous solution to 60° C. so as to allow the reaction between 1-perfluoropropanesulfonyl fluoride and potassium hydroxide to take place.

When the current was stopped after 300 hours had passed from the beginning of the electrochemical fluorination began, 58.5 kg of the reaction solution (gas absorbed solution) within the gas absorption tower was collected. This solution was a colorless and clear solution. Titration analysis of this solution showed that the concentration of potassium hydroxide was 0.4%.

In this fluorination, the proton concentration in the reaction solution changed between 520 and 850 ppm, the total amount of the starting material fed in the electrochemical fluorination reaction was 15.2 kg (120.5 mol), the voltage changed between 5.2 and 6.2 V, the decomposition rate was 2.8% or less, the liquid-to-gas ratio in the gas absorption reaction was 27.9, and the gas absorption rate was 97% or more.

Example 8

The gas absorbed solution produced in Example 7 was placed into a fluorocarbon resin (PTFE)-lining reaction vessel. 3.84 kg (51.9 mol) of a calcium hydroxide powder was added to this gas absorbed solution, and the mixture was heated to 70° C. with stirring.

After the temperature rose, stirring was continued for 2 hours, after which stirring was stopped and the mixture was left to stand overnight, allowing the solid to settle. After this aqueous solution was decanted, the solid was removed by filtration.

75% sulfuric acid was added to the resulting filtrate until the pH reached the range of 7.0 to 7.5 (the amount of addition: 4.74 kg (36.3 mol)) and neutralization was conducted with stirring. Stirring was continued for 1 hour in order to complete the neutralization reaction. One hour later, stirring was stopped and the formed potassium sulfate was allowed to settle by standing. The potassium sulfate was removed by filtration.

The obtained colorless and clear aqueous solution of potassium 1-perfluoropropanesulfonate (46.2 kg) was subjected to concentration and drying to give 14.8 kg of potassium 1-perfluoropropanesulfonate. Ion-chromatography analysis of the product showed that the purity of potassium 1-perfluoropropanesulfonate was 95.8%, the content of sulfate ions was 2.3%, the content of fluoride ions was 220 ppm, the content of chloride ions was 10 ppm, and no potassium hydroxide was detected.

Example 9

Instead of adding 75% sulfuric acid to the filtrate from which the calcium fluoride had been removed by filtration in Example 2, a reaction residue in producing trifluoromethanesulfonic acid by acid decomposition (containing 72% of sulfuric acid, 2% of trifluoromethanesulfonic acid, and 26% of potassium sulfate) was added to 267 kg of the gas absorbed solution until the pH reached the range of 7.0 to 7.5 (the amount of addition: 28.7 kg) and neutralization was conducted. Stirring was continued for 1 hour in order to complete the neutralization reaction. One hour later, stirring was stopped and the insoluble material was removed by filtration.

The colorless and clear aqueous solution of potassium trifluoromethanesulfonate obtained by this filtration (211 kg) was subjected to concentration and drying to give 54.5 kg of potassium trifluoromethanesulfonate. Analysis of the resulting product showed that the purity of potassium trifluoromethanesulfonate was 97.6%, the content of sulfate ions was 1.3%, the content of fluoride ions was 130 ppm, the content of chloride ions was 14 ppm, and no potassium hydroxide was detected.

Example 10

During the electrochemical fluorination reaction in Example 1, about 5 g of a sample of the reaction solution was taken, poured carefully into about 25 g of ice and water, and diluted. A 48% aqueous solution of potassium hydroxide fell into drops to this solution and neutralization was conducted. Subsequently, stirring was continued for 20 minutes in order to complete the neutralization reaction.

About 5 g of the neutralized solution was weighed precisely. As an internal standard, 0.015 g of 1,4-dioxane was weighed precisely, mixed with the aliquot, and the aliquot was subjected to nuclear magnetic resonance ($^1$H-NMR) analysis. The proton concentration in the reaction solution was calculated to be 480 ppm based on the relative integrated intensity of proton in the reaction solution (1.0 to 3.0 ppm) to the integrated intensity of 1,4-dioxane (near 3.7 ppm).

INDUSTRIAL APPLICABILITY

The method of the present invention is suitably applied to processes for producing potassium perfluoroalkanesulfonate and can achieve the simplification of process steps, the reducing of possibilities of environmental pollution and global warming, and the suppression of pipe clogging. In addition, the potassium perfluoroalkanesulfonate according to the present invention can be applied suitably as a starting material for a perfluoroalkanesulfonic acid which is useful as synthetic catalysts in manufacturing pharmaceuticals and allows the prevention of the corrosion of apparatus materials such as glass linings, the suppression of pipe clogging, and the simplification of treatments.

The invention claimed is:

1. A method for producing potassium perfluoroalkanesulfonate, comprising the steps of:
    subjecting an alkanesulfonyl halide compound represented by the general formula: $C_nH_{2n+1}SO_2X$, in which n is an integer of 1 to 3 and X is Cl or F, to electrochemical fluorination in anhydrous hydrogen fluoride, thereby to generate a production gas containing, as the main component, perfluoroalkanesulfonyl fluoride represented by the general formula: $C_nF_{2n+1}SO_2F$ in which n is an integer of 1 to 3, (electrochemical fluorination step);
    reacting the production gas with an aqueous solution of potassium hydroxide, thereby to generate a gas absorbed solution containing a potassium perfluoroalkanesulfonate represented by the general formula: $C_nF_{2n+1}SO_3K$, in which n is an integer of 1 to 3, (gas absorption step);
    removing potassium fluoride, potassium hydroxide, and potassium sulfate which are impurities contained in the gas absorbed solution, (purification step); and
    subjecting the aqueous solution from which the impurities are removed to concentration and drying, thereby to obtain potassium perfluoroalkanesulfonate represented by the general formula: $C_nF_{2n+1}SO_3K$, in which n is an integer of 1 to 3, (concentration and collection step), wherein, in the purification step, alkali metal hydroxide or alkaline earth metal hydroxide is added to the gas absorbed solution to allow it to react with the potassium fluoride contained in the gas absorbed solution so as to form a fluoride precipitate and potassium hydroxide, and an acid is further added to precipitate the potassium hydroxide in the solution, and these precipitates are removed by filtration, said acid is selected from the group consisting of sulfuric acid, perfluoroalkanesulfonic acid, and a residue of the reaction solution generated in producing perfluoroalkanesulfonic acid by an acid decomposition reaction, and in the concentration and collection step, the filtrate is subjected to concentration and drying to obtain potassium perfluoroalkanesulfonate.

2. The method for producing potassium perfluoroalkanesulfonate according to claim 1, wherein an alkanesulfonyl fluoride compound represented by the general formula: $C_nH_{2n+1}SO_2F$, in which n is an integer of 1 to 3, is used as the starting material for the electrochemical fluorination.

3. The method for producing potassium perfluoroalkanesulfonate according to claim 1, wherein in the electrochemical fluorination step, the decomposition rate in the electrochemical fluorination reaction is controlled to less than 3% to suppress the formation of byproducts by maintaining the proton concentration in the reaction solution in the range of 150 to 1,500 ppm.

4. The method for producing potassium perfluoroalkanesulfonate according to claim 1, wherein in the electrochemical fluorination step, the decomposition rate in the electrochemical fluorination reaction is controlled to less than 3% to suppress the formation of byproducts by retaining a reaction temperature of 0 to 18° C. and a current density of 1 to 3 $A/dm^2$ and maintaining the proton concentration in the reaction solution in the range of 150 to 1,500 ppm.

5. The method for producing potassium perfluoroalkanesulfonate according to claim 1, wherein in the gas absorption step, the gas absorbed solution containing potassium perfluoroalkanesulfonate which has a concentration of potassium hydroxide of less than 1% is generated.

6. The method for producing potassium perfluoroalkanesulfonate according to claim 1, wherein in the gas absorption step, the gas absorbed solution containing potassium perfluoroalkanesulfonate is generated by contacting the aqueous solution of potassium hydroxide at a liquid-to-gas ratio of 10 or more relative to the amount of the production gas to be introduced.

7. The method for producing potassium perfluoroalkanesulfonate according to claim 1, wherein in the gas absorption step, an aqueous solution of potassium hydroxide having an initial concentration of potassium hydroxide of 10% or more is employed, and gas absorption is carried out until the concentration of potassium hydroxide reaches less than 1%.

8. The method for producing potassium perfluoroalkanesulfonate according to claim 1, wherein in the purification step, the acid is sulfuric acid, which is used to precipitate the potassium hydroxide in the solution as potassium sulfate.

9. The method for producing potassium perfluoroalkanesulfonate according to claim 1, wherein in the purification step, the acid is perfluoroalkanesulfonic acid, which is used to convert the potassium hydroxide in the solution into potassium perfluoroalkanesulfonate, and the potassium hydroxide is precipitated as the potassium perfluoroalkanesulfonate.

10. The method for producing potassium perfluoroalkanesulfonate according to claim 1, wherein in the purification step, the acid is the residue of the reaction solution generated in producing perfluoroalkanesulfonic acid by an acid decomposition reaction, which is used to neutralize the potassium hydroxide in the solution and to precipitate the potassium hydroxide.

11. A method for producing potassium perfluoroalkanesulfonate comprising the steps of:

subjecting an alkanesulfonyl halide compound represented by the general formula: $C_nH_{2n+1}SO_2X$, in which n is an integer of 1 to 3 and X is Cl or F, to electrochemical fluorination in anhydrous hydrogen fluoride, thereby to generate a production gas containing, as the main component, perfluoroalkanesulfonyl fluoride represented by the general formula: $C_nF_{2n+1}SO_2F$ in which n is an integer of 1 to 3, (electrochemical fluorination step);

reacting the production gas with an aqueous solution of potassium hydroxide thereby to generate a gas absorbed solution containing a potassium perfluoroalkanesulfonate represented by the general formula: $C_nF_{2n+1}SO_3K$, in which n is an integer of 1 to 3, (gas absorption step);

removing potassium fluoride, potassium hydroxide, and potassium sulfate which are impurities contained in the gas absorbed solution, (purification step); and subjecting the aqueous solution from which the impurities are removed to concentration and drying, thereby to obtain potassium perfluoroalkanesulfonate represented by the general formula: $C_nF_{2n+1}SO_3K$, in which n is an integer of 1 to 3, (concentration and collection step), wherein in the purification step, aluminum sulfate is added to the gas absorbed solution to allow it to react with the potassium fluoride and the potassium hydroxide contained in the gas absorbed solution so as to form a precipitate of fluoride, potassium sulfate, or double salt thereof, and the precipitate is filtered off, and in the concentration and collection step, the filtrate is subjected to concentration and drying to obtain potassium perfluoroalkanesulfonate.

* * * * *